United States Patent [19]

Bailey

[11] Patent Number: 5,158,455
[45] Date of Patent: Oct. 27, 1992

[54] CONTROL UNIT FOR A SCALER AND A POLISHER

[75] Inventor: Ronald L. Bailey, Harvester, Mo.

[73] Assignee: Young Dental Manufacturing Company, Earth City, Mo.

[21] Appl. No.: 477,609

[22] Filed: Feb. 9, 1990

[51] Int. Cl.⁵ .............................................. A61C 3/02
[52] U.S. Cl. ..................................... 433/88; 433/216
[58] Field of Search ................. 433/88, 216, 125, 126, 433/27, 28, 98, 119; 51/426, 436

[56] References Cited

U.S. PATENT DOCUMENTS

| | | |
|---|---|---|
| 2,759,266 | 8/1956 | Cassani . |
| 2,876,601 | 5/1956 | McFaddan . |
| 3,163,963 | 10/1963 | Caron . |
| 3,344,524 | 10/1967 | Kulischenko ........................ 433/88 |
| 3,793,778 | 2/1974 | Price . |
| 3,852,918 | 12/1974 | Black . |
| 3,882,638 | 5/1975 | Black . |
| 4,482,322 | 11/1984 | Hain et al. . |
| 4,487,582 | 12/1984 | Warrin . |
| 4,492,574 | 1/1985 | Warrin et al. . |
| 4,494,932 | 1/1985 | Rzewinski . |
| 4,569,161 | 2/1986 | Shipman . |
| 4,648,840 | 3/1987 | Conger, Sr. . |
| 4,820,152 | 4/1989 | Warrin et al. . |
| 4,941,298 | 7/1990 | Fernwood et al. ................... 433/88 |

FOREIGN PATENT DOCUMENTS

| | | |
|---|---|---|
| 0097288 | 1/1984 | European Pat. Off. . |
| 0294548 | 12/1988 | European Pat. Off. . |
| 2588182 | 12/1985 | France . |

Primary Examiner—Gene Mancene
Assistant Examiner—Michael Lynch
Attorney, Agent, or Firm—Polster, Lieder, Woodruff & Lucchesi

[57] ABSTRACT

A control box for both a scaler and an airpolisher wherein the abrasive flow to the airpolisher and the power to the scaler is controlled by a single control knob. Activation of the scaler or polisher handpiece is automatic upon lifting the selected handpiece from its bracket. The polisher portion of the unit includes an abrasive pickup system having a replaceable abrasive container. Air flow within the container is such that the abrasive empties substantially linearly with time.

29 Claims, 5 Drawing Sheets

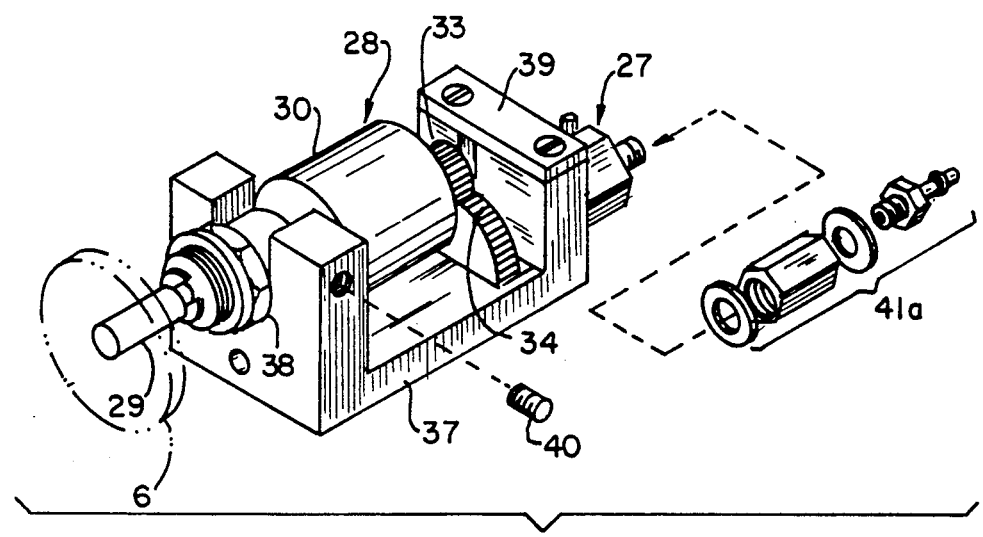
FIG.5.
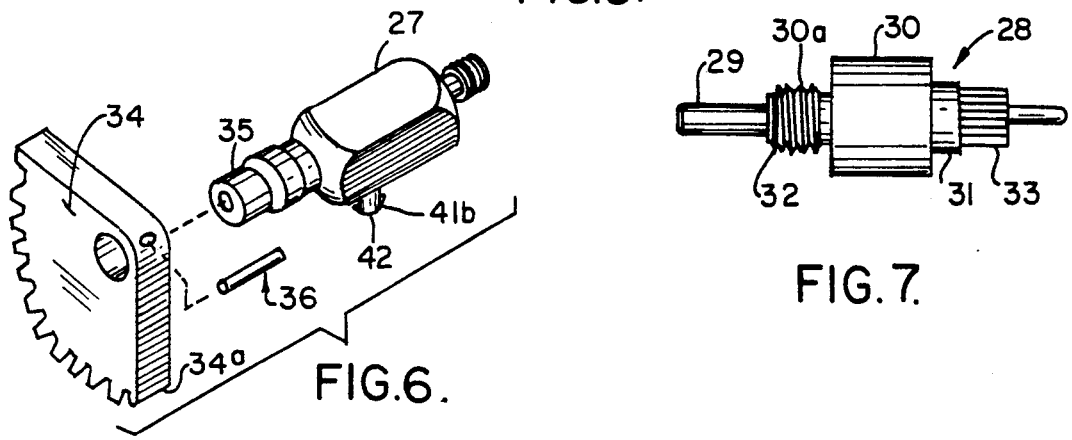
FIG.6.
FIG.7.
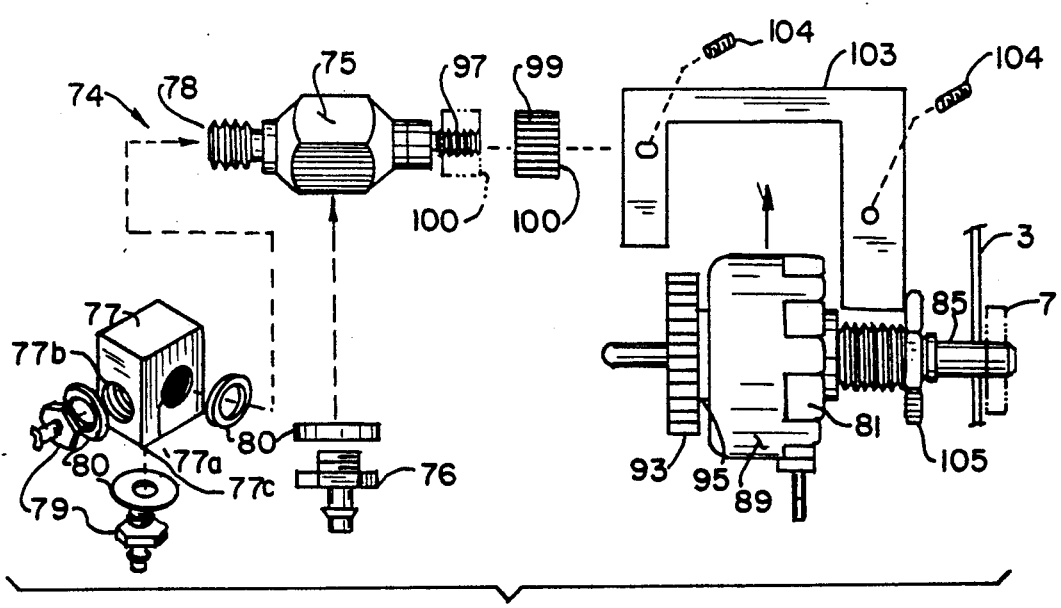
FIG.8.

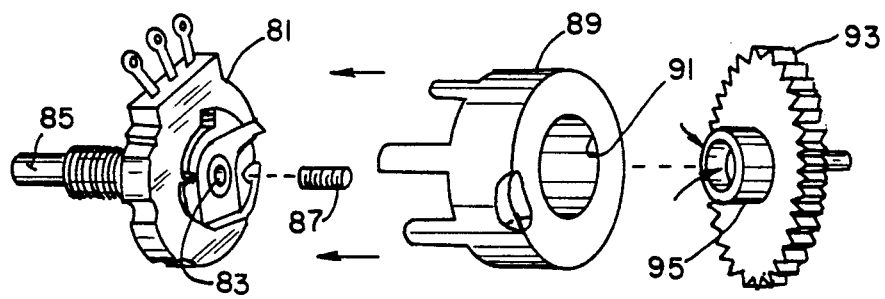
FIG. 9.
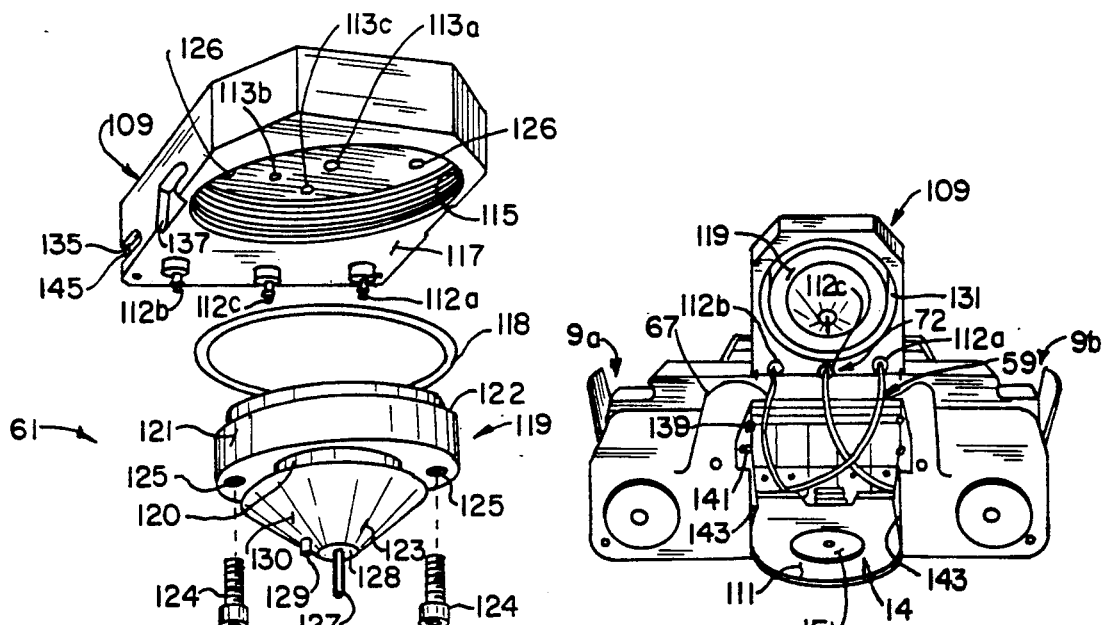
FIG. 11.
FIG. 10.
FIG. 12.

CONTROL UNIT FOR A SCALER AND A POLISHER

BACKGROUND OF THE INVENTION

This invention relates to dental cleaning, and, in particular to a dental cleaning unit which includes both a scaler and an airpolisher wherein the scaler and polisher are controlled from a single control box. It also relates to improvements in the airpolisher portion of the unit.

The use of a scaler and airpolisher to clean teeth is well known in the art. Often dental technicians, hygienists, or dentists (referred to herein collectively as hygienists) will use both a scaler and a polisher on a single patient and will switch between the two devices. Prior art scalers and polishers are often separately controlled. The control box therefore includes multiple controls, which are disadvantageous both because their adjustment requires close attention by the hygienist and because they are are difficult to clean. The control boxes have also been generally bulky and difficult to disinfect.

More recently, U.S. Pat. No. 4,820,152 to Warrin et al shows a single handpiece with interchangeable scaler and polisher heads. With this device, the switching back and forth between the two heads, will cause the junction between the handpiece and the head to become loose and the handpiece and/or the heads will have to be replaced so that there will again be a tight fit. Further, a hygienist will want to do as little switching as possible. Thus, instead of using the scaler and polisher on each tooth as he or she goes along, the hygienist will use the scaler on every tooth and then polish all the teeth with the polisher. By only changing instruments once, instead of cleaning each tooth with both instruments, the patient's teeth will not be cleaned as well.

In prior art airpolishing systems, a jar holding the abrasive must be refilled by pouring the abrasive particles into the jar. Some of these prior art abrasive containers are hoppers having air/abrasive inputs at their bottom. These containers require cleaning at the end of the day in order to prevent the system from clogging To clean the container the hygienist must remove the container, with all its tubes attached, from its control box and follow a series of detailed instructions. This cleaning process is tedious, time-consuming, and messy. Other prior art containers do not empty evenly over time. Rather, they have heavy abrasive flow initially and the flow tapers off as the container empties.

SUMMARY OF THE INVENTION

One of the objects of the present invention is to provide a combination scaler and airpolisher unit having simplified controls.

Another object is to provide such a device wherein the power level to the scaler and the abrasive level to the polisher are controlled by a single manual control.

Another object is to provide such a device having a compact, easily disinfected control box.

Another object is to provide such a scaler/polisher combination wherein a hygienist may freely switch between instruments.

Another object is to provide a simplified and effective abrasive distribution container and cap for an airpolisher.

Another object is to provide such an abrasive container wherein the container may be a disposable jar.

Another object is to provide such a container wherein the container does not need to be cleaned, and the polishing systems can be turned off at the end of the day without additional labor.

Another object is to provide such a container which permits visual inspection of the abrasive level during operation of the device.

Another object is to provide a specially designed jar and support system for the jar which reinforce the jar when it is pressurized and which prevent removal of the jar when it is pressurized.

Other objects of this invention will be apparent to those skilled in the art in light of the following description and accompanying drawings.

In accordance with one aspect of the present invention, generally stated, there is provided an improved control box for a scaler and airpolisher. The control box includes an electrical input for the scaler, an air input and an abrasive supply container for the polisher, and a liquid input for both the scaler and the polisher. The control box has only two control knobs, one to control liquid flow for both the polisher and the scaler, and one to control power to the scaler and to control abrasive pickup for the polisher.

The liquid input communicates with a first valve having an input, a normally open output and a normally closed output. One of the outputs communicates directly with dividing means for directing liquid either to the scaler or the polisher. The other output communicates with the dividing means via a liquid control valve which is operated by the liquid control knob. Preferably, when either the scaler or the polisher is operated in a rinse mode, the liquid by-passes the liquid control valve.

The dividing means is preferably a divider having at least two outputs, one with a normally open valve, the other with a normally closed valve. One of the normally open and normally closed valves communicates with the scaler, the other communicates with the polisher. The valves are electrically controlled so that the liquid will flow only to the selected handpiece.

Preferably, the polisher and scaler are held in switch operating supports and the selected handpiece will operate only when the other handpiece is in its support. The supports are preferably handpiece-specific so that one handpiece cannot be placed in the wrong support, and when the non-selected handpiece is in the wrong support, it is interpreted by the control box as being not in a support.

In accordance with another aspect of the invention, the abrasive container includes an air input, an air-abrasive output, and means for controlling the amount of abrasive delivered to the polisher. The abrasive control means includes a shunt line connected on opposite ends to the air input and the air/abrasive output of the abrasive supply container and an abrasive control valve. The shunt is connected to the output of an abrasive control valve. A three port manifold is connected to the valve input at one of its ports. The remaining ports of the manifold are inserted in the air input line. The abrasive control valve outlet is controlled by the power control knob. The shunt line also provides means for maintaining the pressure at the valve and at the polisher handpiece the same.

In accordance with another aspect of the invention, generally stated, the power control means controls both the abrasive flow in the air polisher and electric power to the scaler. Preferably, the power control means includes an abrasive control valve for the polisher and a potentiometer for the scaler. The abrasive control valve and the potentiometer are interconnected so they can be operated by the power control knob. Preferably, they are so interconnected that the knob turns the potentiometer directly but is geared up to turn the valve approximately several turns for one of the potentiometer. The potentiometer includes a cap covering one side and a shaft which extends through the potentiometer to the capped side thereof. The cap has a hole formed in the center thereof to expose the shaft. The shaft is adapted at the capped side of the potentiometer to carry a drive gear. The shaft preferably has a bore formed therein sized to receive a screw which holds the drive gear. The valve control means includes a gear.

In accordance with another aspect of the invention, generally stated, there is provided a control box for a dental cleaner which cleans with abrasive carried by gas. The control box includes a supply of gas, a container carrying a supply of abrasive, a cap for the container having an inlet and an outlet both of which communicate with the container, and a retaining plate on which the container sits. The abrasive container is preferably replaceable, eliminating the need to pour abrasive into the container when the abrasive is used up. The cap and the retaining plate trap the container between them, to support the bottom of the container and prevent it from rupturing when the container is pressurized. The supply of air communicates with the inlet of the cap, and the outlet communicates with the cleaner. The cap further has an exhaust port which is closed during operation of the handpiece and is opened when operation ceases.

The cap has a downwardly directed frustoconical bottom which points towards the interior of the container. The air inlet is centrally positioned in the cap and includes an extension tube extending just above the highest level to which the container is filled The air/abrasive outlet is offset from the air inlet, on the sloping wall of the frustoconical bottom, and includes an extension tube extending to the plane of the lowermost face of the frustoconical bottom. The inlet and outlet are made smaller than the rest of the piping in the unit, so that the velocity of air through the inlet is increased to provide proper fluffing of the abrasive powder The air creates a toroidal flow of the abrasive/air mixture abrasive powder container and causes a mixture of air and powder to be drawn into the air/abrasive outlet. This arrangement allows for the abrasive container to empty linearly with time.

BRIEF DESCRIPTION OF THE DRAWINGS

FIG. 5 is a perspective, partially exploded view of a water control assembly of the unit of FIG. 1.

FIG. 6 is a perspective exploded view of a water control valve and gear of the control means of FIG. 5

FIG. 7 is a side elevational view of a shaft assembly of the control of FIGS. 5 and 6.

FIG. 8 is an exploded view of a power control assembly of the unit of FIG. 1, for controlling both abrasive flow to a polisher and power to a scaler.

FIG. 9 is an exploded view of a modified potentiometer portion of the power control assembly of FIG. 8.

FIG. 10 is an exploded perspective view of an abrasive pick-up cap assembly of the control unit of FIG. 1.

FIG. 11 is a perspective view of the control unit of FIG. 1, showing the cap assembly open and an abrasive jar removed.

FIG. 12 is a side elevational view of the cap assembly of FIG. 10, showing the locking mechanism which locks the cap in place over an abrasive container.

DESCRIPTION OF THE PREFERRED EMBODIMENT

Figure 1:
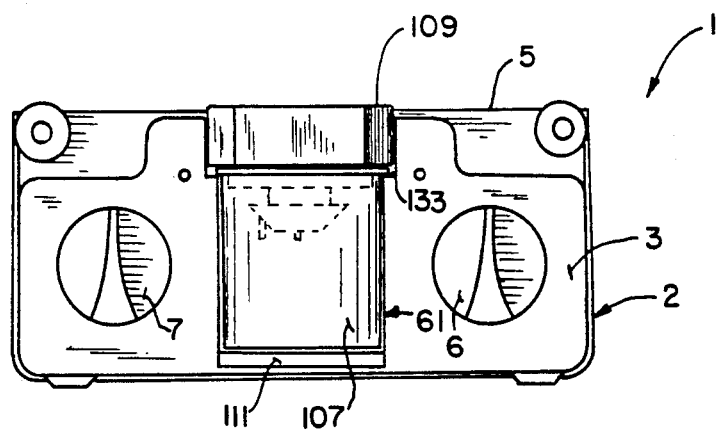
FIG. 1 is a front elevational view of one illustrative embodiment of control unit for a combination scaler and polisher in accordance with the present invention.
Figure 2:
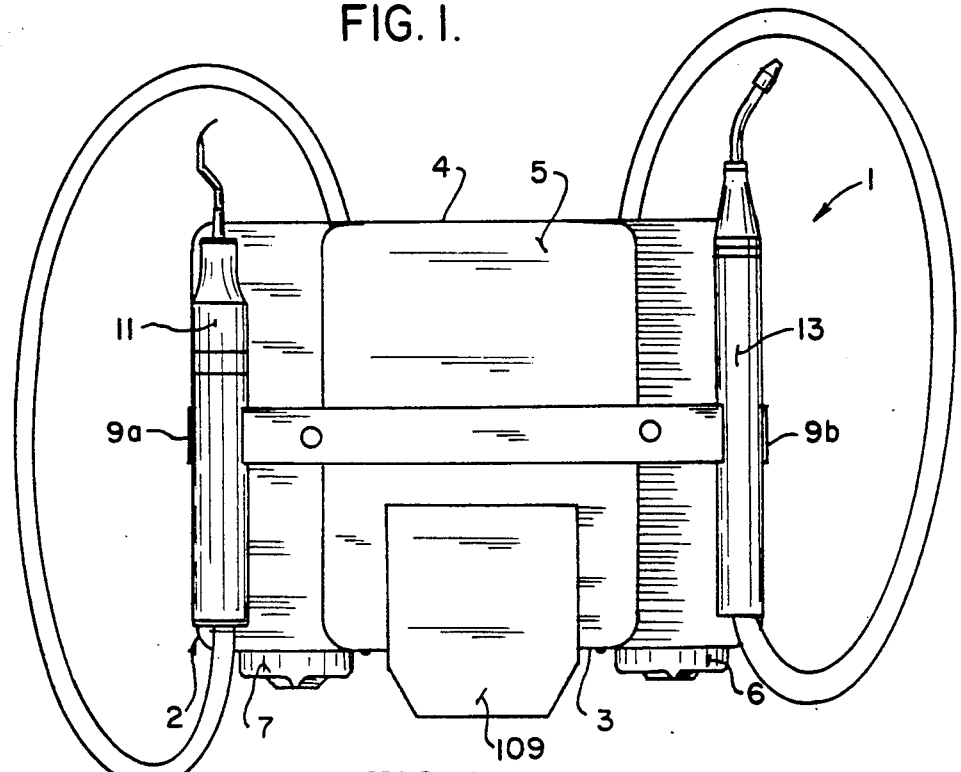
FIG. 2 is a top plan view of the control unit of FIG. 1.

Referring to the FIGS. 1 and 2 reference numeral 1 represents a dental cleaning unit of the present invention operable either in a run mode or a rinse mode. Unit 1 includes a control box 2 having front and back panels, 3 and 4, respectively, and a top panel 5. The box 2 may be quite compact, having a width of 7.5", a depth of 5.5", and a height of 3.375". A pair of control knobs 6 and 7 for controlling fluid flow and power are on front panel 3 A pair of brackets 9a, 9b for receiving a scaler handpiece 11 and an airpolisher handpiece 13 are on top panel 5 An opening 14 in the front of control box 2 (FIG. 11) is sized to receive a jar 107 containing abrasive A source of electricity 15, of liquid 17, and of air 19 lead into control box 2 through back panel 5 for use by the scaler and the polisher. The polisher handpiece is preferably the one disclosed in my copending application, Ser. No. 477,748, filed Feb. 9, 1990.

Figure 3:
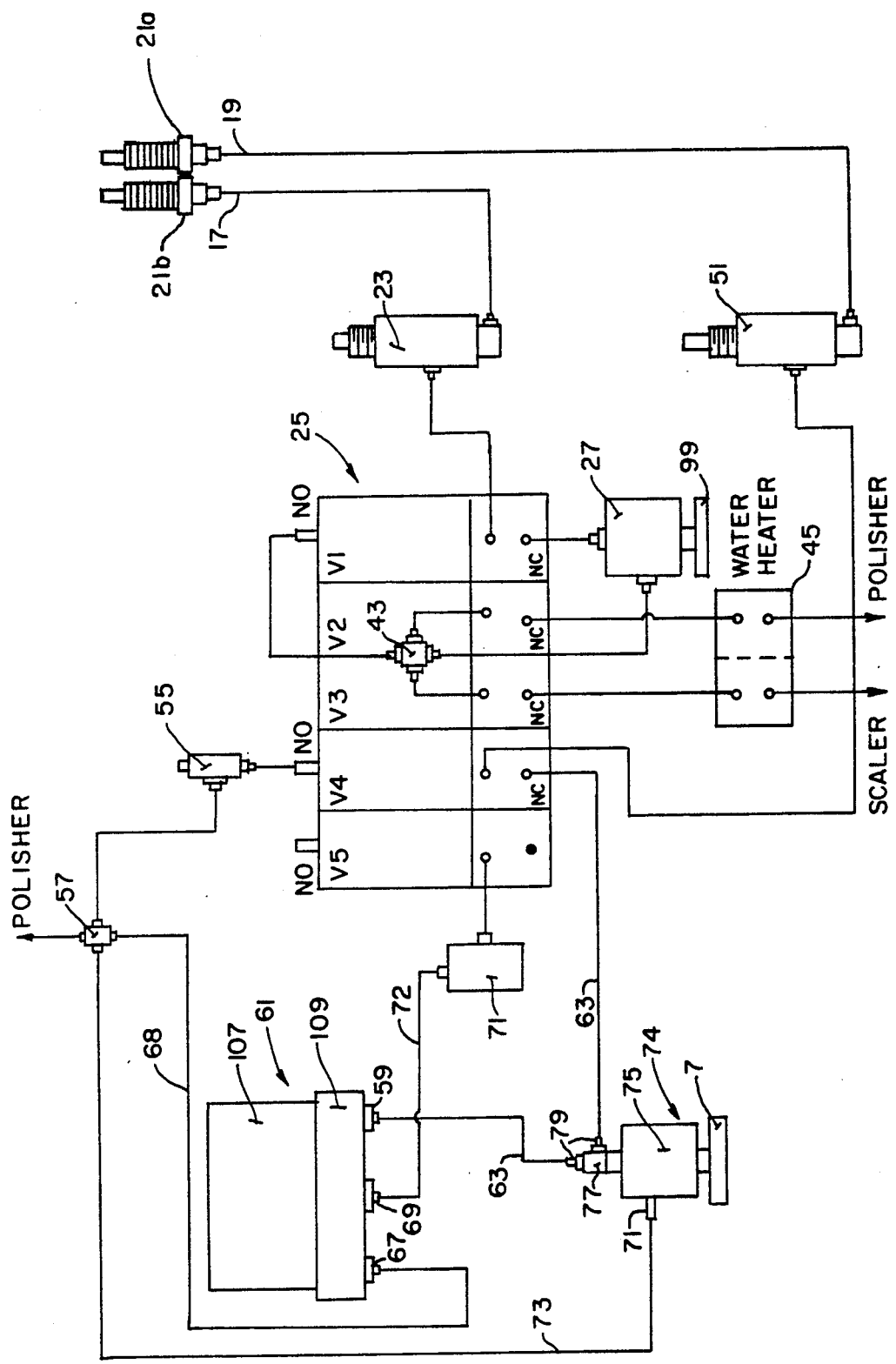
FIG. 3 is a liquid and air flow schematic of the control unit of FIG. 1.

Referring to the fluid flow schematic (FIG. 3), air input 19 and water input 17, enter control box 2 through feed-throughs 21a and 21b in rear panel 5. Water input 17 is connected to a water regulator 23, which keeps the pressure of the water entering the system at a constant 30 psi. The water passes from the regulator to a valve panel 25 containing five electrically controlled valves, $V_1$-$V_5$. Each valve, $V_1$-$V_5$ has a valve input $V_{ni}$, a normally closed outlet $V_{nc}$, and a normally open outlet $V_{no}$. Valves $V_1$-$V_4$ have electrical terminals so that they may be opened and closed by a plurality of relays and contacts as will be explained later. As used herein, when a valve is opened, its normally open output is open and its normally closed output is closed. Conversely, when one of valves $V_1$-$V_5$ is closed, its normally open output is closed and its normally closed output is open.

When in run mode, water enters valve $V_1$ at its input and passes through its normally closed outlet $V_{1c}$ to a valve 27 which adjusts the volume of water flow through the system. Valve 27 is preferably a needle valve, and does not affect the water pressure. Thus, the water pressure is constant throughout the system.

As shown in FIG. 5, water control valve 27 is controlled by control knob 6 by means of a shaft assembly 28. Assembly 28 includes a shaft 29 rotatably carried by a bushing 30 having a threaded sleeve 30a (FIG. 7). Shaft 29 is held in place by a flange 31 integral with shaft 29 and a retaining ring 32 which cooperates with a groove (not shown) in shaft 29 adjacent flange 31. A pinion gear 33 is secured to shaft 29 adjacent flange 31. Control knob 6 is attached to shaft 29 at an end remote from pinion gear 33.

Pinion gear 33 engages a sector gear 34 which is placed on a valve knob 35 of valve 27. A spiral pin 36 is inserted in a hole drilled through gear 34 and valve knob 35 so that gear 34 and knob 35 rotate together Gear 34 is installed on valve 27 with the valve closed and with an edge 34a of gear 34 being substantially parallel to the axis of a lower port 42 of valve 27.

Shaft assembly 28 and valve 27 with gear 34 are mounted in a bracket 37 which holds gears 33 and 34 in meshing contact. Valve 27 and assembly 28 are held in place by a threaded nut 38, a cap 39, and a plurality of set screws 40. Barb fitting assemblies 41a,b are secured to the inlet and outlet of valve 27 so that the water tubing may be attached thereto.

The water flows from valve 27 to a manifold 43. When in rinse mode, the water enters the divider from the normally open output $V_{1o}$ of valve $V_1$, bypassing valve 27.

Manifold 43 directs the water either to valve $V_2$ and the polisher or to valve $V_3$ and the scaler. The water flows to the handpieces from the normally closed outputs $V_{2c}$, $V_{3c}$ of valves $V_2$ and $V_3$, after passing through a water heater 45. Valve 27 may be adjusted so that there is one setting of control knob 6 which provides optimal water flow to both the scaler and the polisher.

Heater 45 has a thermostat 47, a fusible fuse 49, and a resistance coil heater 50. The thermostat 47 preferably has a set point of 150° F. The fuse 50 is preferably set to melt at 190° F.

The air flows through tubing having a constant inner diameter from the air inlet to the polishing handpiece. The air flows from air inlet 19 to an air regulator 51 which keeps the pressure of entering air at a constant 30 psi. The air flows from regulator 51 to the input of valve $V_4$. The normally open output $V_{4o}$ of valve $V_4$ leads to a needle valve 55 and then to a manifold 57 having an output communicating with polisher 13. The air passing through the normally open output of valve $V_4$ constitutes bleed air and as valve 55 is partially closed, the bleed air to the airpolisher is minimal in flow. Unless the air supply is turned off at its source, bleed air will continuously pass through the system to the polisher, when the polisher is not in use.

The normally closed output $V_{4c}$ of valve $V_4$ is connected to an input 59 of an abrasive container assembly 61 by an air line 63. Within abrasive container assembly 61, the air picks up abrasive and exits the container assembly at outlet 67 which is connected to manifold 57 by a conduit 68. Abrasive container 61 has an exhaust outlet 69 which is connected to the input of valve $V_5$ by an exhaust line 72. The normally closed output $V_{5c}$ of valve $V_5$ is blocked and the air exiting valve $V_5$ is exhausted to the atmosphere through its normally open output $V_{5o}$. Output $V_{5o}$ is open only when the polisher is not in use or is in rinse mode. An air filter 71 is inserted in exhaust line 72 to collect whatever abrasive may be in the exhaust so that the abrasive particles will not be exhausted to the atmosphere.

A shunt line 73 connects inlet line 63 and outlet line 68 of container assembly 61 to bypass assembly 61. An abrasive control valve 74 controls the amount of air which bypasses assembly 61 to control the amount of abrasive that is delivered to polisher 13.

Abrasive control valve assembly 74 comprises a needle valve 75 having a barbed fitting 76 connected to its output and a manifold 77 having three ports 77a, b, c connected to its input 78 by manifold port 77a. Barb fittings 79, similar to barb fitting 76, are inserted into the remaining ports 77b, c of manifold 77. Washers 80 are placed at the junctions between valve 75 and barb 76, between valve 75 and manifold 77, and between manifold 77 and barbs 79 to create air-tight seals at these points.

When the amount of air passing through line 63 is altered the amount of air entering container assembly 61 is also altered, thereby changing the amount of abrasive that is picked up in container assembly 61. It will be noted that the volume of air flowing to polisher 13 is not altered Only the ratio of air in the shunt to air in the container assembly is altered The air pressure at the polisher is thus the same as the air pressure at output $V_{4c}$ of valve $V_4$.

As can be seen in FIG. 8, abrasive control valve 75 is controlled by power knob 7 via a modified potentiometer 81. The modified potentiometer has a tapped hole 83 drilled 0.200" deep at the rear of its shaft 85. A screw 87 is threaded and glued into hole 83 so that approximately 0.150" of the screw is exposed. Screw 87 is preferably a 6/32×⅜" set screw. Screw 87 is attached to potentiometer 81 with potentiometer cap 89 removed. Cap 89 has a 7/16" hole 91 machined in its center.

An annular gear 93 is secured to screw 87 by means of an internally threaded drive gear adapter 95 Adapter 95 is securely connected to gear 93 at its center aperture (not shown) such that gear 93 and adapter 95 rotate together The gear-adapter assembly is threaded and secured, as with glue, to screw 87 such that gear 93 will rotate when shaft 87 is turned.

Valve 75 includes a shaft 97 having a pinion gear 99 securely attached thereto, such that its outer edge 100 is 0.175" from a surface 101 of valve 75. Shaft 97 is ground so that its end is flush with outer edge 100 of gear 99 (shown in dotted lines). Gear 99 is placed on shaft 97 when the valve is closed Valve 75 and potentiometer 81 are mounted in a bracket 103 so that gears 99 and 93 mesh. Set screws 104 and nut 105 are used to secure valve 75 and potentiometer 81 in place. Potentiometer shaft 85 protrudes through front panel 3 so that knob 7 may be attached thereto. This arrangement provides for control of both the abrasive flow to polisher 13 and power to scaler 11 by a single knob. The gearing provides about four revolutions of the valve shaft 97 for one revolution of the potentiometer 81. Before valve 75 and potentiometer 81 are connected, they are preferably adjusted so that there is one setting of knob 7 which provides for optimal performance of both handpieces. This eliminates the need for the hygienist to alter the settings when instruments are changed.

Referring to FIG. 10, abrasive container assembly 61 includes an open topped cylindrical container or jar 107, filled with abrasive, positioned between a hinged cap 109 and a retainer base 111. The inlet 63 and outlets 67 and 69 all feed into and out of cap 109. Retainer plate 111 supports the bottom of container 107. The sides of container 107 are circular and can withstand the internal pressure caused by the incoming air. However, the flat bottom cannot. Thus, retainer plate 111 supports the bottom of container 107 to keep it from rupturing.

Cap 109 includes three ports 112a, b, c with which the input, output and exhaust lines, respectively, communicate. Ports 112a, b, c communicate with three orifices 113a, b, c at the top of a threaded recess 115 in the bottom surface 117 of cap 109.

A mixer 119 including a base 121 having a shoulder 122 and a frustoconical portion 123 is securely attached to cap 109 by screws 124. A groove 120 exists between base 121 and portion 123. Screws 124 extend through bores 125 in base 121 to engage holes 126 in cap recess 115. An annular rabbet 122 in base 121 holds an o-ring 118. When the base 121 is screwed to cap recess 115, the o-ring is pushed outward to form a seal for the top of container 107.

Mixer 119 includes a velocity increasing tube 127, extending from the bottom 128 of portion 123 at its center, and a pick-up tube 129 extending down from a sloped side 130 of portion 123. Tube 127 is the air inlet tube and communicates with orifice 113a through an air path in cap 109. Tube 127 extends 0.50" down from bottom 128. Pick-up tube 129 extends down a sufficient distance such that its end lies in the same plane as bottom 128. Pick-up tube 129 communicates with orifice 113b through a second air path in cap 109. The configuration of mixer 119 provides for a toroidal motion of air into the abrasive, upward along the sides of the container 107, around the sloped wall 123 of the mixer 119, and back toward the surface of the abrasive. This motion allows the abrasive to empty linearly with time. In other words, if half the jar were used in five minutes, the other half would also be used up in five minutes if no adjustments are made.

Input pipe 127 has in inner diameter of 0.047", and output pipe 129 has an inner diameter of 0.047". These diameters are both smaller than the 0.062" inner diameter of the internal tubing throughout the system, but larger than the 0.034" inner diameter of the air/abrasive tube in handpiece 13. The use of smaller diameter tubing in container assembly 61 increases the velocity of entering air, increasing the ability of the air to stir up the abrasive within container 107 and to pick up abrasive. This further aids the ability of the jar to empty linearly. Because tubes 63 and 68 are of the same diameter, the smaller diameter of tubes 127 and 129 does not affect the similarity of pressure at valve $V_4$, and the polisher The use of smaller diameter tubing in handpiece 13 increases the velocity of the exiting abrasive The higher velocity of the abrasive makes the cleaning action of the polisher 13 more effective.

Pressure is released through an outlet orifice, not shown, in the base portion 121 within the recess 120. The exhaust outlet opening communicates with the port 112c through orifice 113c. The groove 120 provides a dead air space which is relatively free of abrasive.

Figure 13:
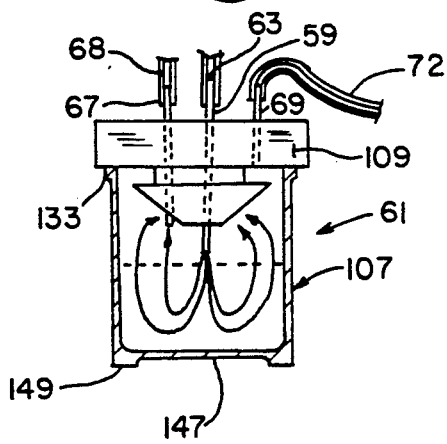
FIG. 13 is somewhat diagramatic view in partial section of the cap assembly of FIG 10.

Mixer 119 is smaller in diameter than threaded recess 115. Thus, there is a channel 131 formed when mixer 119 is secured to cap 109 (FIG. 11). Channel 131 is sufficiently wide so that jar 107 will thread therein. Jar 107 includes a threaded upper portion and a lip 133 (FIGS. 10 and 13) which seat respectively against the O-ring 118 and the bottom of recess 115 when threaded into channel 131.

The use of a cap having a channel into which an abrasive container may fit allows container 107 to be replaceable. Abrasive jar 107 may be shipped pre-filled to the proper depth with the appropriate abrasive powder, preferably a sodium bicarbonate powder of uniform 140 to 200 mesh size, with added flow enhancers and flavorants, in accordance with well-known industry standards. The hygienist may refill the abrasive simply by removing a lid, not shown, from the jar and replacing the empty abrasive jar with a new abrasive jar. This avoids the necessity of having to pour the abrasive into a permanent container.

Because the inlet and outlet tubes lead to and from the cap, rather then to and from the container bottom, the air path is not clogged with abrasive and the need to clean the abrasive jar at the end of a day, as in prior art polishing systems, is obviated. A hygienist may simply turn off the unit at the end of the day.

As shown in FIG. 12, cap 109 has a horizontal slot 135 and a substantially Vertical slot 137, on either side at the back thereof. Slots 135 and 137 cooperate with a pair of pins 139 and 141 on side surfaces 143 of control box opening 14. Slot 135 is elongate so that cap 109 may both pivot around, and slide on, pin 139. A set screw 145 at the back of slot 135 prevents cap 109 from detaching from unit 1. Slot 137 includes a lock path 146 at its top. Pin 141 cooperates with lock path 146 to lock cap 109 in place. To unlock and open cap 109, cap 109 need only be slid forward until pin 141 is out of path 146, at which time cap 109 will be pivotable.

The jar 107 has a recessed bottom wall 147 surrounded by an annular foot 149. The recess is nearly in contact with a raised disk 151 on retainer plate 111 when the jar is secured to cap 109 and the cap is closed and locked with pins 139 and 141. The bottom of jar 107 is thinner than the sides. Thus, when the jar is pressurized, the bottom bulges outwardly sufficiently to contact the raised disk 151 and pushes the cap upward against the pins 139 and 141. The cap 109 and disk 151 thus provide support for the jar 107 and prevent its bottom from rupturing. The side walls of the jar have been found to withstand substantial overpressures for long periods of time. When it is pressurized, the jar also prevents the cap from being pulled forward, and thereby locks it in place during operation of the airpolisher.

Figure 4:
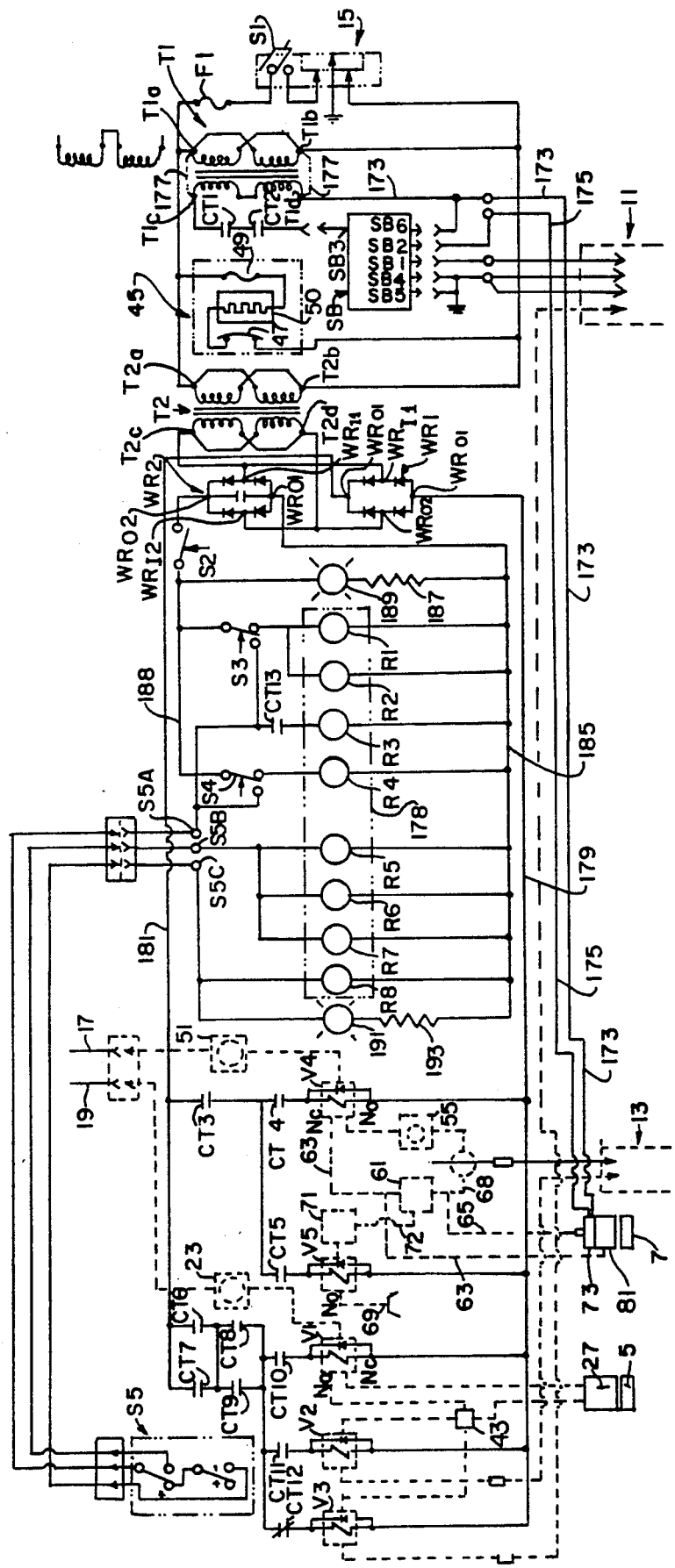
FIG. 4 is an electrical schematic of the device of FIG. 1, including liquid and air flow.

FIG. 4 shows the electrical circuitry of unit 1. A power switch S1 controls power to the unit as a whole. In a 110 volt system, water heater 45 is connected in parallel with switch S1. In a 220 volt system, a step-down transformer is substituted for the heater 45. The primary coils of a first transformer T1 and a second transformer T2 are also connected in parallel with switch S1. All the circuitry within control box 2 is 12 V except for scaler board SB. A fuse F1 is serially connected to switch S1 to cut off power to unit 1 if blown. Transformers T1 and T2 each have four ports T1a-T1d and T2a-T2d.

The secondary coils of transformer T1 are connected to a removable scaler board SB which controls the vibrational motion of the tip of scaler 11. Scaler board SB has six ports SB1-SB6. Transformer port T1c is connected to third port SB3 of scaler board SB via a pair of normally open contacts CT1 and CT2 to supply power to board SB. Transformer port T1d is connected to the input of potentiometer 81 and scaler board port SB6 over an electrical wire 173. The output of potentiometer 81 is connected to scaler board port SB2 by an electrical wire 175. Scaler board ports SB1 and SB4 are connected to scaler 11 and ports SB4 and SB5 are connected to ground.

A pair of jumper wires 177 (shown as dotted lines) may be installed across corresponding terminals of the primary and secondary coils of transformer T1 if it is not going to be used.

Transformer T2 is a step down transformer and drops the line voltage to 12 V. The secondary coils of transformer T2 are connected to a pair of full wave rectifiers WR1 and WR2 which are connected in parallel. Transformer port T2c connects transformer T2 to first inputs of rectifiers WR1 and WR2. Port T2d is connected to second inputs of both rectifiers WR1 and WR2.

Rectifiers WR1 and WR2 each have first and second outputs $WR_{01}$ and $W_{02}$, respectively, which are connected to valves $V_1$-$V_5$ and a relay board 178, having eight relays $R_1$-$R_8$, which control valves $V_1$-$V_5$ and scaler board SB. First output $WR_{01}$ of rectifier WR1 is connected to a first terminal of each valve $V_1$-$V_5$ via an electrical wire 179. The second output of rectifier WR1 is connected to a second terminal of valves $V_1$-$V_5$ by a wire 181 and a plurality of contacts CT3 -CT12 to control the opening and closing of valves $V_1$-$V_5$. Contacts CT3-CT11 are normally open contacts; contact CT12 is a normally closed contact.

The contacts affect the opening and closing of various valves according to the following table:

| Valve | Controlling Contacts |
| --- | --- |
| $V_1$ | CT6, CT7, CT8, CT9, CT10 |
| $V_2$ | CT6, CT7, CT8, CT9, CT11 |
| $V_3$ | CT6, CT7, CT8, CT9, CT12 |
| $V_4$ | CT3, CT4 |
| $V_5$ | CT3, CT5 |

Contact CT3 is connected in series with contacts CT4 and CT5 to control valves $V_4$ and $V_5$. Contacts CT4 and CT5 are connected in parallel.

Contacts CT6-CT9 are connected to form a block 183 which controls valves $V_1$-$V_3$ with contacts CT10, CT11, and CT12 respectively. In block 183, contacts CT6 and CT7 are connected in parallel, as are contacts CT8 and CT9. Contacts CT6 and CT7 are each connected in series with contacts CT8 and CT9. Thus, power will be delivered to valves $V_1$-$V_3$ as long as one of contact CT6 or CT7 is closed and one of contacts CT8 or CT9 is closed.

A thirteenth contact CT13, is placed in series with relay R3. CT13 is a normally open contact. All the contacts are opened and closed by activation and deactivation of relays R1- R8, each relay controlling specific contacts, and thus specific valves and the scaler board, according to the following table:

| Relay | Contacts controlled | Devices Controlled |
| --- | --- | --- |
| R1 | CT3, CT6 | $V_1$-$V_5$ |
| R2 | CT11, CT12 | $V_2$, $V_3$ |
| R3 | CT2 | SB |
| R4 | CT7, CT13 | $V_1$-$V_3$ |
| R5 | CT1, CT4 | $V_4$, SB |
| R6 | CT5, CT8 | $V_1$-$V_3$, $V_5$ |
| R7 | CT10 | $V_1$ |
| R8 | CT9 | $V_1$-$V_3$ |

When a relay is activated, it will close its associated normally open contacts, or open its associated normally closed contacts.

Output $WR_{01}$ of rectifier WR2 is connected to a first port of each relay R1-R8 along a wire 185. Output $WR_{02}$ of rectifier WR2 is connected to a jar interlock switch S2. Switch S2 is closed when cap 109 carrying container 107, is closed. If the container is not in place or is not closed, switch S2 will be open and neither the scaler nor the polisher will be operative.

A wire 188 connects a pair of switches S3 and S4 in parallel with each other and in series with switch S2. A power indicator light 189 and a 510 Ohm, 1 Watt resistor 187 are serially connected between wires 185 and 188 before switch S2. Light 189 indicates that power is running through relay board 178. Switches S3 and S4 are normally open switches operated by brackets 9b and 9a which hold scaler handpiece 11 and polisher handpiece 13, respectively. When scaler handpiece 11 is in its bracket, switch S3 is open. The switch is closed when the scaler handpiece is removed from its bracket. Switch S4 is opened and closed by polisher 13 in the same manner.

A two stage foot control switch S5, of the type commonly found in dental operatories, is serially connected to switches S3 and S4 and to contact CT13. Switch S5 has three ports S5a, S5b, and S5c, corresponding to its two stages: rinse and run. As will be explained below, when the foot pedal is depressed to run position, water will flow to control valve 27 and air will flow to control valve 75, if the polisher is selected. When in rinse mode, water will bypass valve 27 and air will bypass valve 75. Only bleed air will be sent to the polisher when the system is in rinse mode or the scaler is being used. Bleed air will continue to be delivered to the airpolisher when the power to unit 1 is switched off at switch S1.

Port S5a is connected to the closed position terminal of switch S3, the open position terminal of switch S4, and to contact CT13. Port S5c is connected to relay R8 and a rinse indicator light 191 connected in series with a 510 Ohm, 1 Watt resistor 193. Port S5b is connected to relays R5, R6, and R7.

With the scaler handpiece in its bracket, the polisher handpiece up and the foot pedal in its second, run, position, switch S3 will be opened, switch S4 will be closed, and relays R1, R2, R5, R6, and R7 will be activated. Relays R2, R6, and R8, will close contacts CT6, CT8, CT10, and CT11, and open contact CT12, opening valve $V_1$ to direct water to needle valve 27, and opening valve $V_2$ and closing valve $V_3$ to direct water from divider 35 to polisher 13. Contact CT11 is normally open and contact CT12 is normally closed. Both are controlled by relay R2. Thus, when one is opened, the other is closed. In this manner the water is directed to the proper handpiece.

Relays R1 and R5 will close contacts CT3 and CT4 thereby opening valve $V_4$ and allowing the air to flow to jar assembly 61 and valve 75. Relays R1 and R6 close contacts CT3 and CT5 to close valve $V_5$, closing the exhaust line 72 from container assembly 61 so that the air in assembly 61 will not be exhausted to the atmosphere. If the exhaust were to remain open, the air entering the jar would escape, interfering with the ability of the system to pick up abrasive particles.

When the foot pedal is lifted to its first position, the polisher will be placed in rinse mode. Relays R1 and R2 will remain activated. Relays R5, R6, and R7 will be deactivated and Relay R8 will be activated. Indicator light 191 will light to inform the hygienist he or she is in rinse mode. Deactivation of relay R5 will close the normally closed output of valve $V_4$ *and* open its normally open output to allow bleed air to pass through to polisher 13. Air will no longer be directed to assembly 61. Deactivation of relay R6 will open the normally open output of valve $V_5$ and the air in assembly 61 will be vented to the atmosphere and jar 107 will be depressurized.

Deactivation of contact R7 will open contact CT10 to close the normally closed output of valve $V_1$ and open its normally open output, directing water directly to manifold 43, bypassing valve 27. All the water will go to polisher 13 and the operator will have no control over water flow. In rinse mode, essentially only water is delivered to handpiece 13. Bleed air is also being delivered, however the quantity of air, as compared to water, is quite small.

When the scaler 11 is lifted, polisher 13 is in bracket 9b and the foot pedal is in run mode, switch S3 will be closed, switch S4 will be open and relays R4, R5, R6, and R7 will be activated. Relay R4 will close contact CT13 to activate relay R3. Relays R4 and R6 close contacts CT7 and CT8 and relay R7 closes contact CT10 to open the normally closed outlet of valve $V_1$ to direct the water to manifold 43 via valve 27. Because relay R2 is not activated, contact CT11 will close and contact CT12 will open, opening the normally closed output of valve $V_3$ and closing the normally closed output of valve $V_4$, thereby directing water from manifold 43 to scaler 11. Relays R5 and R3 close contacts CT1 and CT2 to allow current to flow to scaler board SB to operate scaler 11. Relay R1 is not activated and the normally open output of valve $V_5$ remains open, and bleed air continues to pass through the polisher 11.

When foot pedal S5 is lifted to its rinse position, relay R5, R6, and R7 are deactivated. Deactivation of relay R5 opens contact CT1 cutting off power supply to scaler board SB thereby stopping the vibrational motion of the tip of scaler 11 Relay R8 will be activated, and as before, rinse indicator light 191 will light and the water will bypass valve 27 and pass through the normally open output of valve $V_1$ to manifold 43 and then to scaler 11.

As has been indicated, the first step of foot pedal S5 is rinse and the second step is run. Therefore, whenever either handpiece is used, the handpiece must go through the rinse mode when it is activated and when it is deactivated. This momentary rinse of the polisher 13 will remove abrasive particles that may be in its tip.

The relay-contact system is designed such that neither handpiece will operate if both the handpieces are up or both are down. If scaler 11 and polisher 13 are up, none of relays R1, R2, R3, or R4 will be activated. Relays R1 and R2 are needed for air flow and to direct water flow. Relays R3 and R4 are needed to run the scaler board SB. When both handpieces are down, no current can run to relays R1, R2, or R4, and because relay R4 must be activated to activate relay R3, relay R3 is not activated. Thus, the system will not operate. Therefore, a selected handpiece will operate when it and only it is lifted. Brackets 9a and 9b are handpiece specific. Thus, if a handpiece is in the improper bracket and the other is up, it is as if both handpieces are up, and neither will operate.

Numerous variations within the scope of the appended claims will be apparent to those skilled in the art. For example, a medicinal solution could be used instead of water. Valve 74 could be placed in shunt line 73 rather than at the junction of shunt 73 and the input line 63 to container assembly 61. This would eliminate the need for three port manifold 77. Alternatively, valve 74 could be placed in input line 63 between the shunt input line junction and the container assembly. The shaft extending from the uncapped portion of the potentiometer could be adapted to carry drive gear 93. These variations are merely illustrative.

I claim:

1. A control box for a dental cleaner which cleans with a soluble abrasive powder carried by gas, said control box including a supply of gas and a container assembly, the container assembly comprising a container carrying a supply of abrasive, said container including imperforate bottom and side wall means and being open at its top, and a cap for said container, said cap releasably holding said top of said container above the level of said abrasive in said container and having inlet means and outlet means both of which communicate with said container, said supply of gas communicating with said container solely through said inlet means of said cap and said outlet means communicating with said cleaner.

2. The control box of claim 1, wherein said cap has a downwardly directed, generally frustoconical bottom portion.

3. A control box for a dental cleaner which cleans with a soluble abrasive powder carried by gas, said control box including a supply of gas and a container assembly, the container assembly comprising a container carrying a supply of abrasive, said container including imperforate bottom and side walls and being open at its top, and a cap for said container, said cap releasably holding said top of said container above the level of said abrasive in said container and having an inlet and an outlet both of which communicate with said container, said supply of gas communicating with said inlet of said cap and said outlet communication with said cleaner; said cap having a downwardly directed, generally frustoconical bottom portion; said gas inlet being positioned on a lower face of said bottom portion and said outlet being positioned on a sloped side of said bottom.

4. The control box of claim 3, wherein said abrasive container assembly is so configured that it empties generally linearly with time without change in gas pressure or flow.

5. A control box for a dental polisher which cleans with a soluble abrasive powder carried by gas, said control box including a supply of gas and a container assembly, the container assembly comprising a container carrying a supply of abrasive, said container including imperforate bottom and side walls and being open at its top;

a cap for said container, said cap releasably holding said top of said container above the level of said abrasive in said container and having an inlet and an outlet both of which communicate with said container, said supply of gas communicating with said inlet of said cap through a gap supply line and said outlet communicating with said polisher; and means for maintaining gas pressure at said polisher and in said gas supply line the same and for controlling abrasive flow to said polisher, said pressure maintaining means including a shunt connecting said inlet and outlet and a control valve controlling the amount of gas passing through said shunt.

6. The control box of claim 5 wherein said control valve includes an input, an output, and a three-port manifold connected to said inlet by one of its port, said a valve being connected to said gas supply line by the remaining ports of said three-port manifold; said shunt being connected to said outlet of said control valve.

7. A control box for a dental cleaner which cleans with a soluble abrasive powder carried by gas, said control box including a supply of gas and a container assembly, the container assembly comprising a container carrying a supply of abrasive, said container including imperforate bottom and side wall means and being open at its top, and a cap for said container, said cap releasably holding said top of said container above the level of said abrasive in said container and having an inlet and an outlet both of which communicate with said container, said supply of gas communicating with said inlet of said cap and said outlet communicating with said cleaner, said cap further having an exhaust port, said port being closed during operation of said handpiece and being opened when operation ceases.

8. A control box for a dental cleaner which cleans with a soluble abrasive powder carried by gas, said control box including a supply of gas and a container assembly, the container assembly comprising a container carrying a supply of abrasive, said container including imperforate bottom and side walls and being open at its top;

a cap for said container, said cap releasably holding said top of said container above the level of said abrasive in said container and having an inlet and an outlet both of which communicate with said container, said supply of gas communicating with said inlet of said cap and said outlet communicating with said cleaner; and a retaining plate upon which said container sits, said container being trapped between said cap and said retaining plate to prevent internal pressure within said replaceable container from rupturing said container.

9. The control box of claim 8 wherein the container is a jar having a has a recessed bottom wall surrounded by an annular foot.

10. The control box of claim 9 wherein said retaining plate includes a raised disk and wherein the bottom of the jar is nearly in contact with the raised disk when the jar is unpressurized and presses against said disk when the jar is pressurized.

11. The control box of claim 8 wherein the cap is supported by a frame for sliding movement with respect to the frame, the cap being locked against sliding movement by expansion of the jar when the jar is pressurized.

12. A control box for a dental cleaner which cleans with a soluble abrasive powder carried by a gas, said control box including:
 a base;
 a container assembly comprising a container which sits on said base, said container carrying a supply of abrasive, and a cap for said container, said cap releasably holding said container;
 a supply of gas in communication with said container assembly; and
 pressure means for expanding said container to lock said container assembly in place during use.

13. The control unit of claim 12 wherein said cap is slideably connected to said control box, said pressure locking means comprising an annular foot around the periphery of the bottom of said container and a raised disk on said base, said foot surrounding said disk, such that when said control unit is not in operation, the bottom of said container is not in contact with said disk and when said control unit is in operation, the bottom of said container expands to contact said disk trapping said container between said cap and said base.

14. A container assembly for use with a dental cleaner which cleans with a soluble abrasive powder carried by a gas, said container assembly being in communication with a source of gas and said dental cleaner, said container assembly comprising a container, a soluble abrasive in the container, and a cap, said cap including a downwardly directed frustoconical mixer having a sloped side wall and a generally flat bottom, a gas inlet, communicating with said source of gas, on said bottom, and an outlet, communication with said dental cleaner, on said side wall, said mixer creating a toroidal motion of air which stirs said abrasive powder such that said abrasive powder empties generally linearly with time.

15. The container assembly of claim 14 wherein said inlet includes an inlet tube which extends downwardly from said mixer bottom toward but not into said soluble abrasive in said container.

16. The container assembly of claim 15 wherein said outlet includes an outlet tube which extends downwardly a distance sufficient such that the bottom of said outlet tube lies in the same plane as said mixer bottom.

17. The container assembly of claim 15 wherein said inlet tube increases the velocity of gas from said gas supply into said container, increasing the ability of said gas to stir the abrasive powder in said container, thereby facilitating the linear emptying of said abrasive powder from said container over time.

18. The container assembly of claim 14 wherein said inlet and outlet have the same inner diameter.

19. In a dental cleaner which cleans with a soluble abrasive powder carried by a gas, the dental cleaner comprising in combination, a control box, a container of soluble abrasive, a source of gas, and a dental cleaning tip, the improvement wherein said container of soluble abrasive is replaceable without inverting the container; said replaceable container of soluble abrasive having an imperforate bottom, imperforate side wall means, and a threaded upper lip; said control box comprising securing means, above the level of said abrasive in said container, for replaceably securing said replaceable container of soluble abrasive to said control box and placing said container in communication with said source of gas and said dental cleaner, said securing means being the sole means for placing said container in communication with said source of gas.

20. The improvement of claim 19 further including a base upon which said container rests, said base having a raised disk, said container having an annular foot beneath said container bottom which surrounds said raised disk.

21. In a dental cleaner which cleans with a soluble abrasive powder carried by a gas, the dental cleaner comprising in combination, a control box, a container of soluble abrasive, a source of gas, and a dental cleaning tip, the improvement wherein said container of soluble abrasive is replaceable without inverting the container; said replaceable container of soluble abrasive having an imperforate bottom, imperforate side wall means, and a threaded upper lip; said control box comprising means, above the level of said abrasive in said container, for replaceably securing said replaceable container of soluble abrasive to said control box and placing said container in communication with said source of gas and said dental cleaner; said securing and communicating means including a cover which replaceably receives said container, said cover being slideably and pivotally connected to said control box, said cover including an inlet path therethrough which places said container in communication with said source of gas and an outlet path which places said container in communication with said dental cleaner.

22. The improvement of claim 21 wherein said control box includes a first pin and a second pin, said cover including an elongate slot which engages said first pin so that said cover may slide between an inward and an outward position along, and pivot about, said pin, and a second slot which engages said second pin, such that when said cover is in an outward position said cover may be pivoted to replaceably receive said container, and when said cover is in an inward position, said cover is prevented from pivoting.

23. The improvement of claim 21 further including a base upon which said container rests, said base having a raised disk, said container having an annular foot beneath said container bottom which surrounds said raised disk, wherein when said dental cleaner is used, said container is pressurized to cause said container bottom to deform downwardly and to contact said base raised disk such that said container assembly is raised upwardly urging said cover slots against said container box pins to frictionally prevent said cover from sliding from said inward position to said outward position, thereby locking said container in said control box during operation of said dental cleaner.

24. A method for replacing soluble abrasive in a dental air polisher comprising an air polisher cleaning tip, a container of soluble abrasive, and cap means above said container, said cap means having inlet means and outlet means for placing said container in communication with a source of gas; said method comprising:
removing said container from beneath said cap means;
unsealing a fresh pre-filled container of soluble abrasive; and
attaching said fresh container of soluble abrasive beneath said cap means.

25. The method of claim 24 wherein said dental air polisher comprises a control box and a flexible tube connecting the air polisher cleaning tip to the control box, said cap means being connected to said control unit, said cap means having inlet means and outlet means for placing said container in communication with said source of gas and said cleaning tip.

26. The method of claim 25 wherein said cap means is moveably connected to said control unit;
said removing step comprising moving said cap means from an operating position to a container-removing position before removing said emptied container from beneath said cap means;
said method further comprising moving said cap means from said container-removing position to said operating position.

27. The method of claim 26 wherein said moving steps comprise sliding said cap means between said operating position and said container-removing position; said step of sliding said cap means comprising sliding said cap means outwardly from said control unit during said removing step.

28. The method of claim 27 wherein said moving step further includes pivoting said cap means upwardly when said cap means is in said outward, container-removing position to facilitate removal and replacement of said container.

29. The method of claim 24 wherein said container is threadedly connected to said cap means; said step of removing said emptied container from beneath said cap means and placing a fresh container of soluble abrasive beneath said cap means comprising threadedly disconnecting said emptied container from, and threadedly connecting said fresh container to, said cap means.

* * * * *

UNITED STATES PATENT AND TRADEMARK OFFICE
CERTIFICATE OF CORRECTION

PATENT NO. : 5,158,455

DATED : October 27, 1992

INVENTOR(S) : Ronald L. Bailey

It is certified that error appears in the above-identified patent and that said Letters Patent is hereby corrected as shown below:

Col. 4, Line 45, is "valves v1-v4" should be --valves v1-v5--;

Col. 9, Line 4, is "$WR_{01}$ and $W_{02}$" should be --$WR_{01}$ and $WR_{02}$--;

Col. 12, Claim 3, Line 28, is "outlet communication" should be --outlet communicating--;

Col. 14, Claim 14, Line 8, is "communication with" should be --communicating with--.

Signed and Sealed this

Fifth Day of October, 1993

*Attest:*

BRUCE LEHMAN

*Attesting Officer*    *Commissioner of Patents and Trademarks*